United States Patent
Nemechek

(10) Patent No.: US 11,123,560 B1
(45) Date of Patent: Sep. 21, 2021

(54) METHODS OF TREATING COVID-19 INDUCED CYTOKINE STORM

(71) Applicant: Patrick M. Nemechek, Buckeye, AZ (US)

(72) Inventor: Patrick M. Nemechek, Buckeye, AZ (US)

( * ) Notice: Subject to any disclaimer, the term of this patent is extended or adjusted under 35 U.S.C. 154(b) by 0 days.

(21) Appl. No.: 16/895,376

(22) Filed: Jun. 8, 2020

(51) Int. Cl.
*A61N 1/36* (2006.01)
*A61N 1/04* (2006.01)

(52) U.S. Cl.
CPC ....... *A61N 1/36036* (2017.08); *A61N 1/0456* (2013.01); *A61N 1/0472* (2013.01); *A61N 1/36034* (2017.08)

(58) Field of Classification Search
CPC .............. A61N 1/36036; A61N 1/0456; A61N 1/0472; A61N 1/36034
See application file for complete search history.

(56) References Cited

U.S. PATENT DOCUMENTS

| | | | |
|---|---|---|---|
| 6,838,471 B2 | 1/2005 | Tracey | |
| 7,079,888 B2 | 7/2006 | Oung et al. | |
| 7,499,748 B2 | 3/2009 | Moffitt et al. | |
| 7,529,579 B2 | 5/2009 | Colombo et al. | |
| 8,676,324 B2 | 3/2014 | Simon et al. | |
| 8,706,223 B2 | 4/2014 | Zhou et al. | |
| 8,788,034 B2 | 7/2014 | Levine et al. | |
| 8,868,177 B2 | 10/2014 | Simon et al. | |
| 8,914,114 B2 | 12/2014 | Tracey et al. | |
| 9,162,064 B2 | 10/2015 | Faltys et al. | |
| 9,211,409 B2 | 12/2015 | Tracey et al. | |
| 9,211,410 B2 | 12/2015 | Levine et al. | |
| 9,414,219 B2 | 8/2016 | Shao et al. | |
| 9,415,220 B1 | 8/2016 | Spinelli et al. | |
| 9,457,187 B2 | 10/2016 | Zhao et al. | |
| 10,335,396 B2 | 7/2019 | Nemechek | |
| 2017/0043160 A1* | 2/2017 | Goodall | G16H 20/30 |
| 2017/0087364 A1* | 3/2017 | Cartledge | H04R 1/10 |
| 2018/0117017 A1* | 5/2018 | Nemechek | A61K 31/437 |
| 2020/0230408 A1* | 7/2020 | Errico | A61N 1/0456 |
| 2020/0238085 A1* | 7/2020 | Khodaparast | A61N 1/0492 |

OTHER PUBLICATIONS

Tsaava et al., Serum cytokine levels are modulated by specific frequencies, amplitudes, and pulse widths of vagus nerve stimulation, https://doi.org/10.1101/2020.01.08.898890; pp. 1-20, dated Jan. 9, 2020.

Tsaava et al., Specific vagus nerve stimulation parameters alter serum cytokine levels in the absence of inflammation, Bioelectronic Medicine, pp. 1-10, 2020.

Borovikova et al., Vagus nerve stimulation attenuates the systemic inflammatory response to endotoxin, www.nature.com, vol. 405, pp. 458-462, May 25, 2020.

Straube et al., Treatment of chronic migraine with transcutaneous stimulation of the auricular branch of the vagal nerve (auricular t-VNS): a randomized, monocentric clinical trial, The Journal of Headache and Pain, 9 pages, (2015) 16:63.

Bernik et al., Cholinergic antiinflammatory pathway inhibition of tumor necrosis factor during ischemia reperfusion, Journal of Vascular Surgery, pp. 1232-1236, Dec. 2002.

* cited by examiner

*Primary Examiner* — Catherine M Voorhees
(74) *Attorney, Agent, or Firm* — Procopio, Cory, Hargreaves & Savitch LLP

(57) ABSTRACT

Provided herein are methods for preventing, reducing or reversing cytokine storm in a subject in need thereof.

3 Claims, 7 Drawing Sheets

METHODS OF TREATING COVID-19 INDUCED CYTOKINE STORM

TECHNICAL FIELD

The invention relates to methods for preventing, reducing or reversing cytokine storm in a subject in need thereof.

INTRODUCTION

The automatic nervous system (ANS) regulates "involuntary" organs. The ANS includes the sympathetic nervous system and the parasympathetic nervous system. The sympathetic nervous system is affiliated with stress and the "fight or flight response" to emergencies. The parasympathetic nervous system is affiliated with relaxation and the "rest and digest response." The ANS maintains normal internal homeostasis and works with the somatic nervous system. Autonomic balance reflects the relationship between parasympathetic and sympathetic activity.

Vertebrates achieve internal homeostasis during infection or injury by balancing the activities of proinflammatory and anti-inflammatory pathways. However, in many disease conditions, this internal homeostasis becomes out of balance. For example, endotoxin (lipopolysaccharide, LPS) produced by Gram-negative bacteria activates macrophages to release cytokines that are potentially lethal.

Inflammation and other deleterious conditions (such as septic shock caused by endotoxin exposure) are often induced by pro-inflammatory cytokines, such as tumor necrosis factor (TNF; also known as TNF-alpha or cachectin), interleukin (IL)-1.alpha., IL-1.beta., IL-6, IL-8, IL-18, interferon, platelet-activating factor (PAF), macrophage migration inhibitory factor (MIF), and other compounds. These pro-inflammatory cytokines are produced by several different cell types, and contribute to various diseases and disorders through their release during an inflammatory cytokine cascade. When the immune response becomes uncontrolled, e.g., as a result of SARS-CoV-2 infection, and the like, cytokine storm can ensue resulting in adverse consequence, including death.

Accordingly, there is a need in the art for reducing and/or reversing cytokine storm in COVID-19 patients.

SUMMARY

Provided herein are methods for preventing, reducing or reversing cytokine storm in a subject in need thereof, said method comprising: administering to said subject an effective amount of vagus nerve stimulation (VNS). In particular embodiments, the cytokine storm is caused by a condition selected from the group consisting of: a virus, bacteria, graft-versus-host disease, cytomegalovirus infection, Epstein-Barr virus-associated hemophagocytic lymphohistiocytosis, group A streptococcus, influenza virus, variola virus, severe acute respiratory syndrome coronavirus (SARS-CoV), multiple sclerosis, pancreatitis, multiple organ dysfunction syndrome, lung infections, gastrointestinal tract infections, urinary tract infections, central nervous system, infections, skin infections, joint spaces infections, or any substance that is foreign to the body. In a particular embodiment, the cytokine storm is caused by SARS-COV2 infection.

In particular embodiments, the VNS can be provided transcutaneously using electrical stimulation through an electrical current. In one embodiment, the electrical stimulation is achieved by clipping electrodes across the tragus (FIG. 7) or concha (FIG. 6) of an ear and inducing an electrical current with a transcutaneous electrical nerve stimulation (TENS) unit. In particular embodiments, the electrical current has a frequency in the range selected from the group consisting of: about 0.1 Hz to about 30 Hz, about 0.3 Hz to about 25 Hz, about 0.5 Hz to about 20 Hz, about 0.7 Hz to about 15 Hz, about 0.9 Hz to about 10 Hz, about 1.0 Hz to about 9 Hz, about 1.2 Hz to about 8 Hz, about 1.4 Hz to about 7 Hz, about 1.6 Hz to about 6 Hz, or about 2 Hz to about 5 Hz. In particular embodiments, the electrical current has a pulse width in the range selected from: about 20 to about 1000 uS, about 30 to about 900 uS, about 40 to about 800 uS, about 50 to about 700 uS, about 60 to about 600 uS, about 70 to about 500 uS, about 80 to about 450 uS, about 90 to about 400 uS, about 100 to about 350 uS, about 110 to about 325 uS, about 120 to about 300 uS, about 130 to about 275 uS, about 140 to about 260 uS, and about 150 to about 250 uS. In certain embodiments, the electrical current is in a range selected from: about 0.1 to about 5.0, about 0.2 to about 4.0, about 0.3 to about 3.0, about 0.4 to about 2.0, or about 0.5 to about 1.0 mAmps. In a particular embodiment of the invention, the electrical current has a frequency at 2-5 Hz, pulse width at 150-250 uS and 0.5-1.0 mAmps.

In certain embodiments, the electrical stimulation doses can range from a time selected from the group consisting of: about 30 sec to about 5 min; from about 45 sec to about 4.5 mins; about 1 min to about 4 min; about 1.5 to about 3.5 min; about 2 min to about 3 min; about 30 sec to about 5 min; from about 30 sec to about 4.5 mins; about 30 sec to about 4 min; about 30 sec to about 3.5 min; about 30 sec to about 3 min; about 30 sec to about 2.5 min; about 30 sec to about 2 min; about 30 sec. to about 1.5 min; and about 30 sec to about 1 min. The number of doses or treatments per day can be selected from the group consisting of 1, 2, 3, 4, 5, 6, 7, 8, 9, 10, 11, 12, 13, 14, 15, 16, 17, 18, 19, and 20. In other embodiments the number of doses or treatments can range from 1-50 per day.

The method of claim 9, wherein the length of treatment can be from 1 to 30 days, 1 to 25 days, 1 to 20 days, 1 to 15 days, 1 to 10 days, 1 to 5 days. In a particular embodiment, the length of treatment is 14 days. In another embodiment, the subject receives 4, 5-minute treatments per day for 14 days.

DETAILED DESCRIPTION

Provided herein are methods for preventing, reducing or reversing cytokine storm in a subject in need thereof, said method comprising: administering to said subject an effective amount of vagus nerve stimulation (VNS).

The invention methods provided herein are believed to be safe, non-invasive, portable, and do not require certified technicians. The invention methods of preventing, reducing or reversing cytokine storm are extremely effective for immune modulation and recovery of autonomic function from a detrimental SAR-COV-2 infection. The treatment of cytokine storm (also known in the art and used herein as "hyperinflammatory syndrome" and "cytokine release syndrome"), and any condition mediated by cytokine storm, is within the scope of the invention methods provided herein. As used herein, the phrase "preventing, reversing or reducing cytokine storm" (or "hyperinflammatory syndrome" and "cytokine release syndrome") refers to the combined effect of the invention treatment methods to modulate and/or substantially reduce the levels of pro-inflammatory cytokines to within a protective range avoiding pro-inflammatory responses and, on the other hand, avoiding immunosuppression. In particular, VNS was shown to rebalance the working point of autonomic regulation of the immune system into a protective range avoiding pro-inflammatory responses and, on the other hand, avoiding immunosuppression. The "working point" is defined as the magnitude of innate immune responses relative to the infection or injury stimulus. Chronic changes can unfavorably increase or decrease the working point with the resulting overshooting immune response (with tissue damage, sepsis, or even death) or immunosuppression (with secondary infections), respectively.

Figure 1:
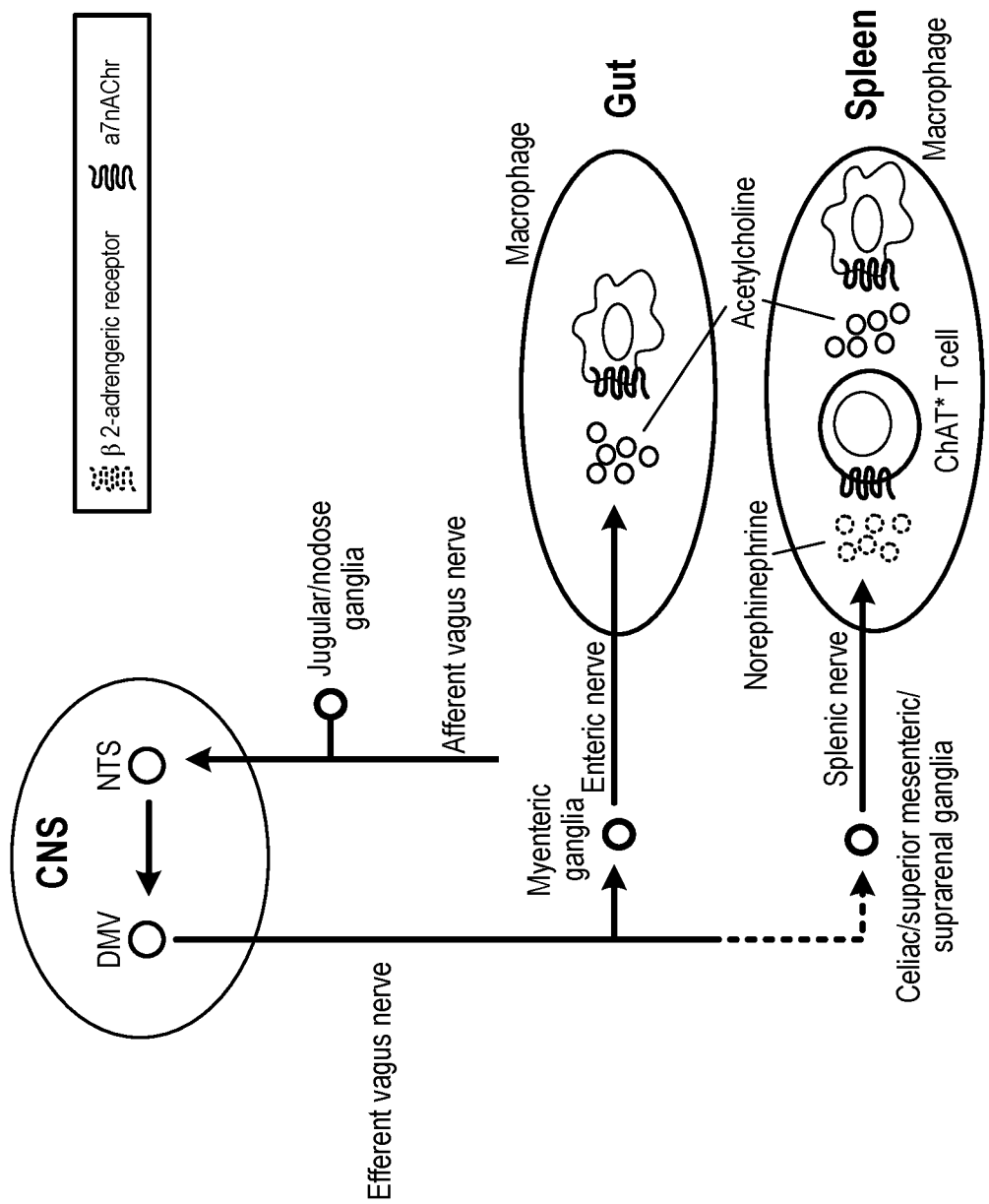
FIG. 1 shows a model of a Vagus Inflammatory Reflex.
Figure 2:
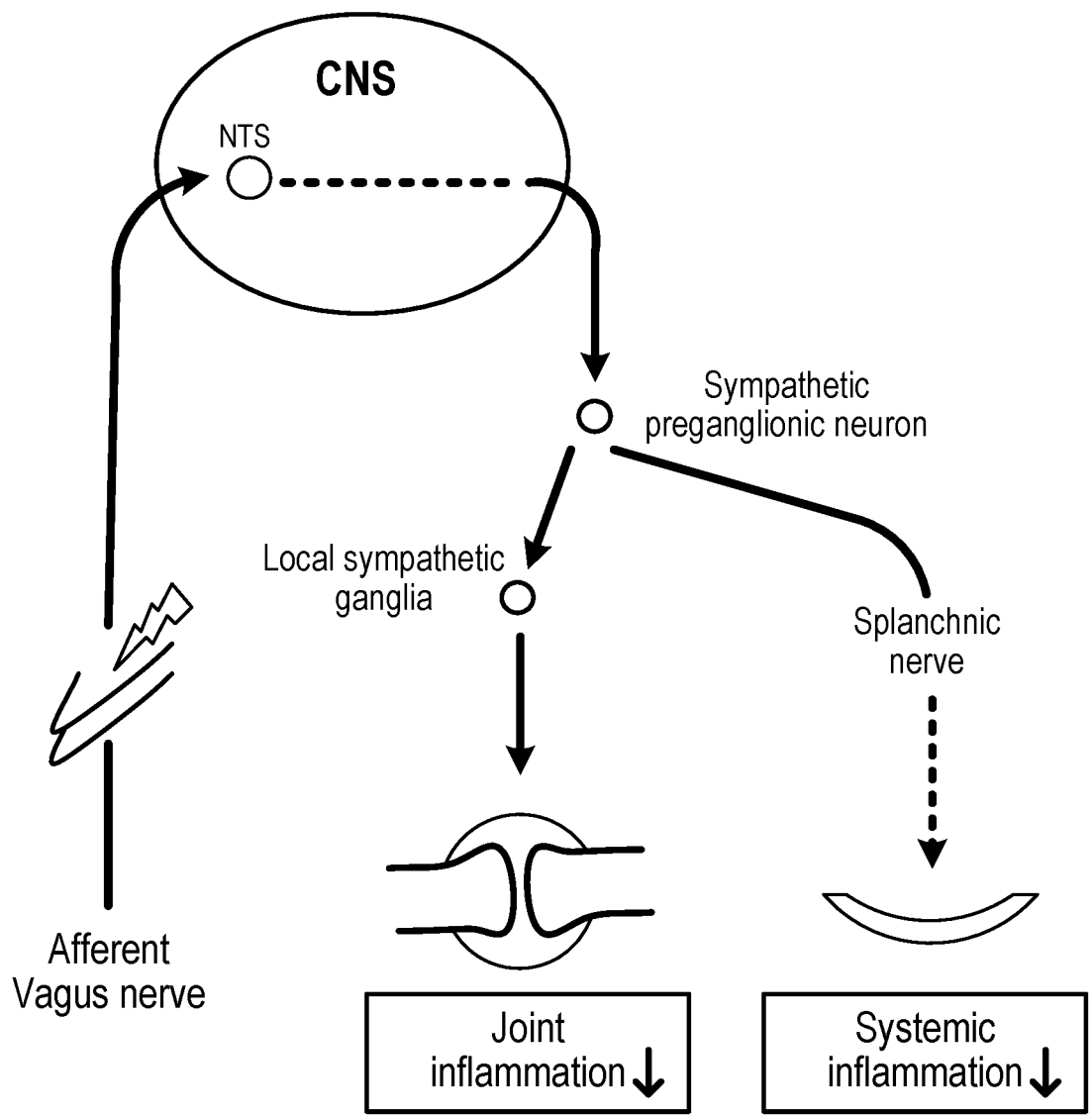
FIG. 2 shows a model of an Anti-inflammatory Sympathetic Reflex.
Figure 3:
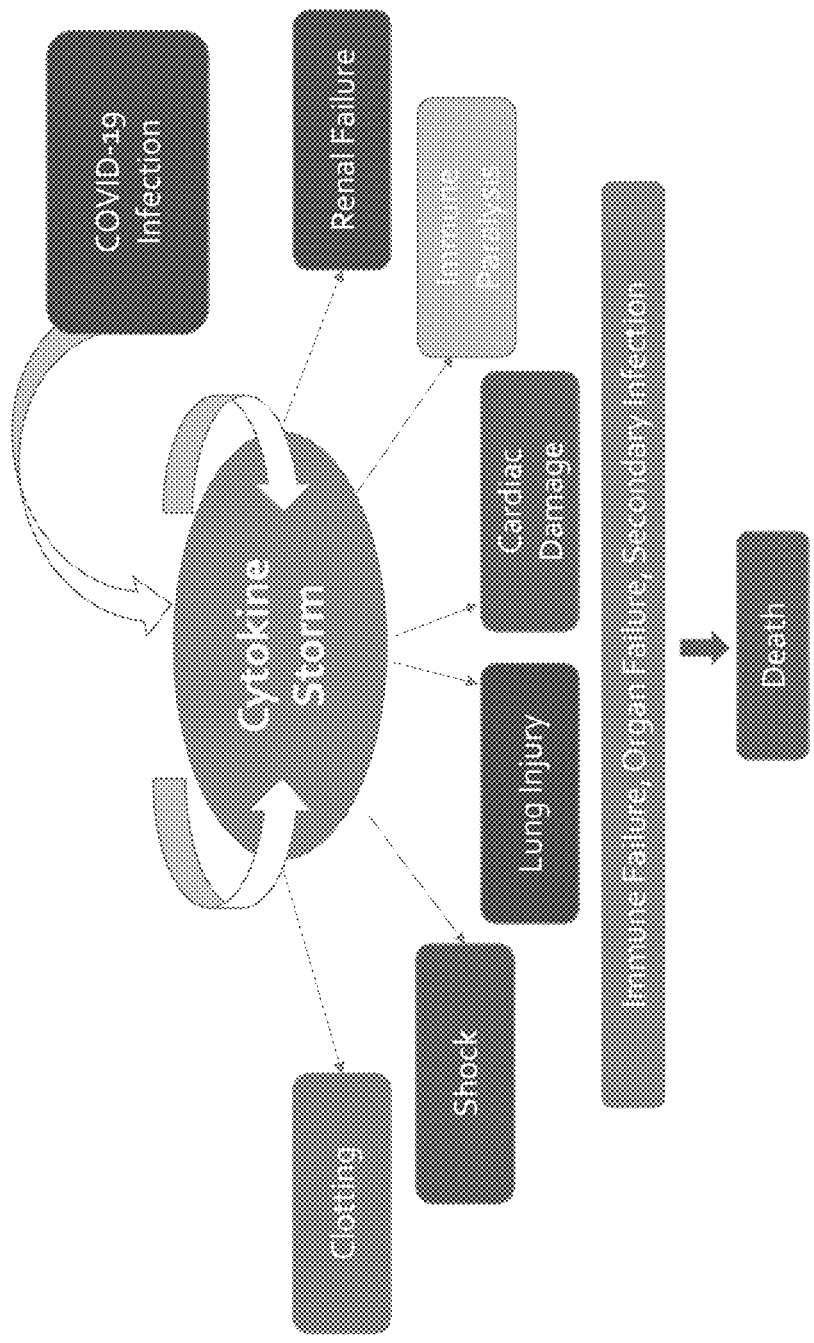
FIG. 3 shows a depiction of how COVID-19 triggers Cytokine Storm and Organ Dysfunction.
Figure 4:
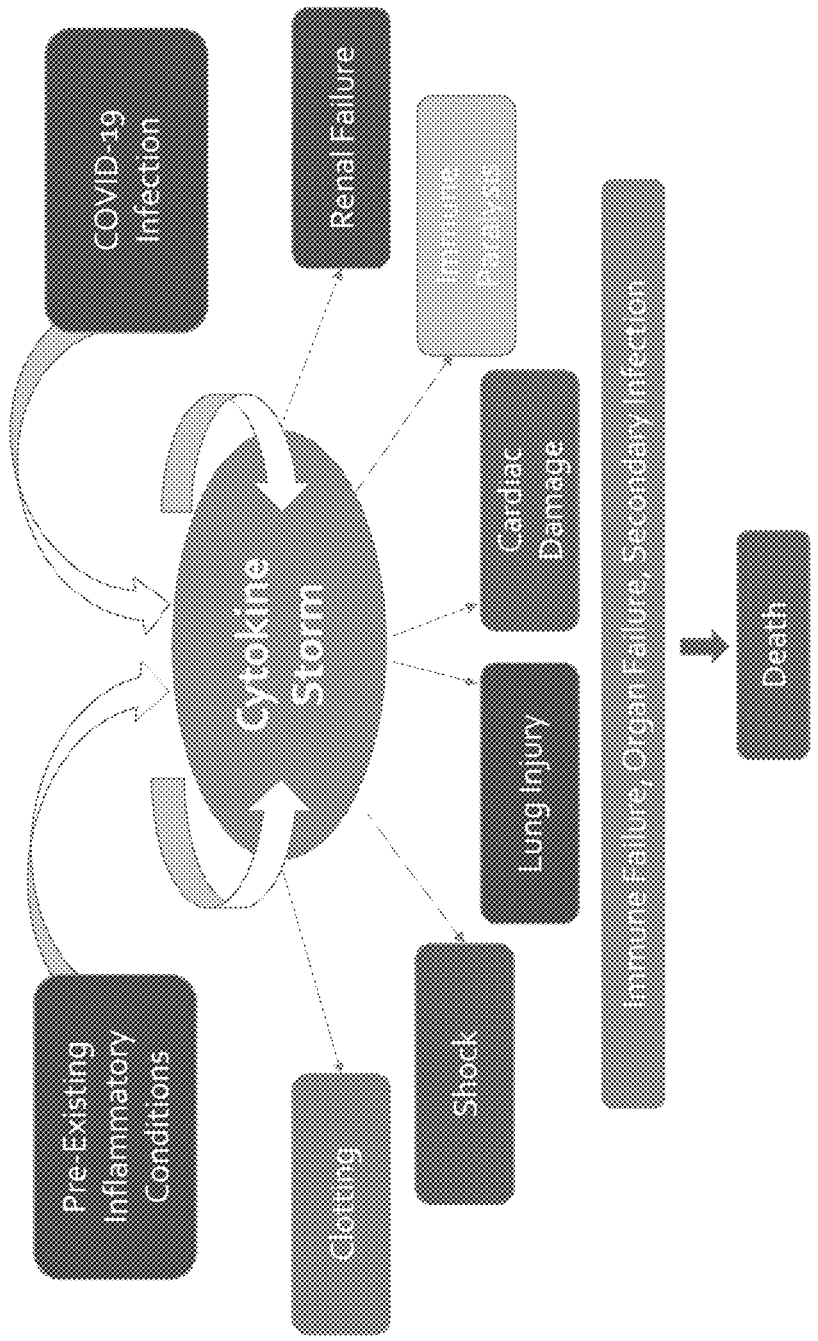
FIG. 4 shows a depiction of how pre-existing conditions worsen Cytokine damage.
Figure 5:
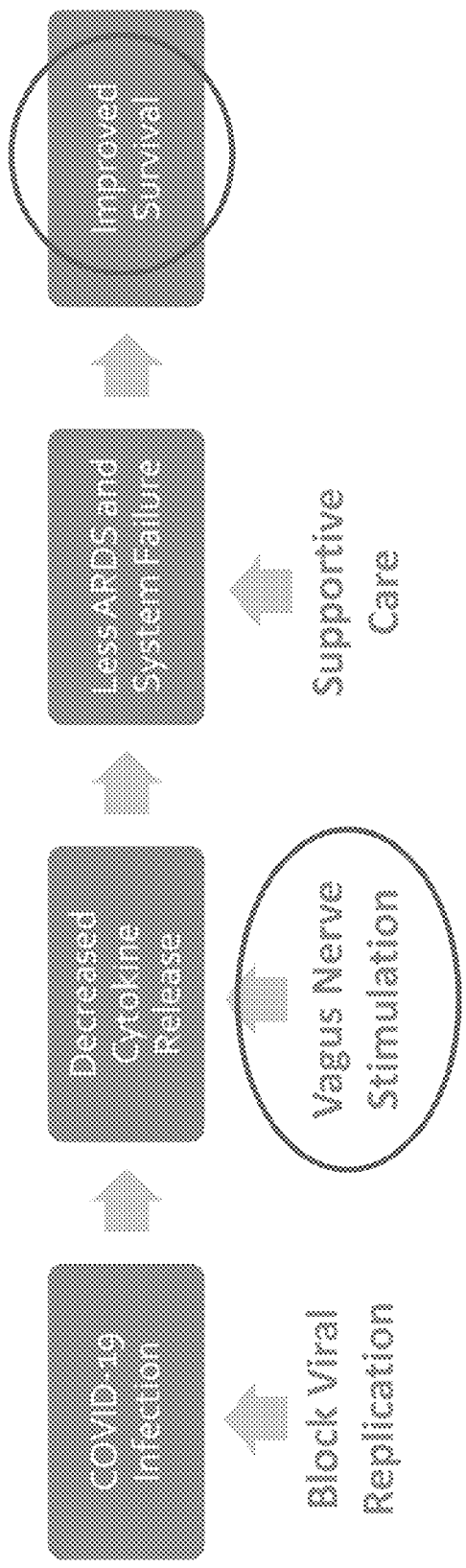
FIG. 5 shows a depiction of improved survival outcome using VNS in combination with antiviral therapy.

Stimulation of the afferent pathway of the vagus nerve can modulate inflammation through 2 separate pathways, the inflammatory reflex (FIG. 1) and the anti-inflammatory sympathetic reflex (FIG. 2). The inflammatory reflex is triggered when the afferent vagus nerve senses inflammatory products through the receptors. The nerve activity is relayed through the central nervous system (CNS) to the efferent vagus nerve. The original pathway involves the splenic nerve although a direct connection between the efferent vagus nerve and the splenic nerve is still controversial. Activated splenic nerves release norepinephrine from their terminals, which interacts with β2-adrenergic receptors expressed on the choline acetyltransferase (ChAT)-positive T cells in the spleen, causing acetylcholine (ACh) release from this specific T cell subpopulation. ACh binds to α7 nicotinic acetylcholine receptors (α7nAChRs) expressed on macrophages residing in close proximity to ChAT-positive T cells, resulting in suppression of proinflammatory cytokine production (e.g., TNFα) by macrophages and alleviated inflammation in many pathological settings (e.g., endotoxemia, septic shock, acute kidney injury).

Another anti-inflammatory pathway elicited by afferent vagus nerve stimulation is shown in FIG. 2. Afferent vagus nerve stimulation can elicit an anti-inflammatory pathway involving sympathetic efferent pathways through the central nervous system (CNS). In a model of joint inflammation, the local release of norepinephrine from sympathetic nerve terminals within joints alleviates inflammation. On the other hand, the splanchnic sympathetic nerve seems to be important to suppress systemic inflammation after lipopolysaccharide (LPS) administration. Direct target(s) of the splanchnic nerve is not clear.

In certain embodiments, the present invention methods relate to the reversal of acute and chronic autonomic dysfunctionby the suppression of pro-inflammatory cytokines, namely interleukin-1 (IL-1), interleukine-6 (IL-6) and tumor necrosis factor-alpha (TNF-alpha). The pro-inflammatory cytokines are reduced through the cumulative effect of reversing intestinal bacterial overgrowth, normalizing dietary intake of omega-6 and omega-3 fatty acids, supplementation with oleic acid, intermittent restriction of caloric intake, and stimulation of the acetylcholine inflammatory reflex by transcutaneous vagal nerve stimulation (tVNS). If this proves initially inadequate, additional steps to reduce pro-inflammatory cytokines include supplementation with curcumin and/or the introduction of carbohydrate restriction and/or intermittent fasting.

As used herein, the phrase "cytokine storm" refers to an overproduced and unregulated immune response that releases excess amounts of cytokines in your body. Under a normal immune response, non-excess amounts of cytokines are released by cells of your immune system to help fight infection. In the case of cytokine storm, the reaction becomes uncontrolled, and it is believed that too many immune cells are activated in a single location causing cytokine storm, which can lead to multi-organ failure, systemic coagulopathy and a high risk of sepsis or death. A cytokine storm is best exemplified by severe lung infections, in which local inflammation spills over into the systemic circulation, producing systemic sepsis, as defined by persistent hypotension, hyper- or hypothermia, leukocytosis or leukopenia, and often thrombocytopenia. In some cases, persistent tissue damage without severe microbial infection in the lungs also is associated with a cytokine storm and clinical manifestations that mimic sepsis syndrome.

Cytokine storms can be caused by a wide variety of infectious and noninfectious diseases; and also result from attempts at therapeutic intervention. In some embodiments, the cause of cytokine storm can be from an exaggerated immune response to a new virus (such as SARS-COV-2, and the like), bacteria, or any substance that is foreign to the body. Other well-known causes of cytokine storm include, for example, graft-versus-host disease, cytomegalovirus infection, Epstein-Barr virus-associated hemophagocytic lymphohistiocytosis, group A streptococcus, influenza virus, variola virus, and severe acute respiratory syndrome coronavirus (SARS-CoV), multiple sclerosis, pancreatitis, or multiple organ dysfunction syndrome. In addition to lung infections, the cytokine storm is a consequence of severe infections in the gastrointestinal tract, urinary tract, central nervous system, skin, joint spaces, and other sites.

Inflammation associated with a cytokine storm begins at a local site and spreads throughout the body via the systemic circulation. Rubor (redness), tumor (swelling or edema), calor (heat), dolor (pain), and "functio laesa" (loss of function) are the hallmarks of acute inflammation. When localized in skin or other tissue, these responses increase blood flow, enable vascular leukocytes and plasma proteins to reach extravascular sites of injury, increase local temperatures (which is advantageous for host defense against bacterial infections), and generate pain, thereby warning the host of the local responses. These responses often occur at the expense of local organ function, particularly when tissue edema causes a rise in extravascular pressures and a reduction in tissue perfusion. Compensatory repair processes are initiated soon after inflammation begins, and in many cases the repair process completely restores tissue and organ function. When severe inflammation or the primary etiological agent triggering inflammation damages local tissue structures, healing occurs with fibrosis, which can result in persistent organ dysfunction.

Acute lung injury (ALI) is a common consequence of a cytokine storm in the lung alveolar environment and systemic circulation and is most commonly associated with suspected or proven infections in the lungs or other organs (Rubenfeld G D, et al. 2005. Incidence and outcomes of acute lung injury. N. Engl. J. Med. 353:1685-1693). Pathogen-induced lung injury can progress into ALI or its more severe form, acute respiratory distress syndrome (ARDS), as seen with SARS-CoV and influenza virus infections.

The symptoms of a cytokine storm are high fever, swelling and redness, extreme fatigue and nausea. At the same time, there can be organ failure with lung failure, ARDS, kidney failure and cardiovascular collapse or shock.

As used herein, the phrase "vagus nerve stimulation" or "VNS" refers to the stimulation of the auricular branch of the vagus nerve. The vagus nerve can be stimulated using methods well known in the art, including internally via a transplanted device (e.g., U.S. Pat. No. 9,211,410; incorporate herein by reference in its entirety), mechanically, or transcutaneously. Transcutaneous vagus nerve stimulation (tVNS) of the auricular branch of the Vagus nerve results in the reduction of pro-inflammatory cytokines via the cholinergic anti-inflammatory pathway (Lerman et al., Neuromodulation 19:283-291, 2016; incorporated herein by reference in its entirety). As used herein, the term "vagus nerve" is used in its broadest sense, and includes any nerves that branch off from the main vagus nerve, as well as ganglions or postganglionic neurons that are connected to the vagus nerve. The vagus nerve is also known in the art as the parasympathetic nervous system and its branches, and the cholinergic nerve. The advantages of vagus nerve stimulation over the use of pharmaceutical agents are set forth in Table 1.

TABLE 1

| Pharmaceutical Agents | Vagus Nerve Stimulation (VNS) |
| --- | --- |
| Few Options | Effective |
| Corticosteroids, NSAIDS | Human and animal data |
| Anti-cytokine specific drugs | Regulates cytokine release |
| Expensive | Safe |
| Increased Risk of Infections | No increased risk of infections |
| Anti-TNF agents increase the risk of bacterial, viral, and fungal infections | Improves inflammation regulation |
| Corticosteroids and JAK inhibitors reduce anti-viral type-I interferon | Does not "suppress" immune system |
| IL-6 inhibitors increase bacterial infection risk | Transcutaneous Stimulation (tVNS) Simple; minimal training Inexpensive; easily manufactured Reusable |

In certain other embodiments, the vagus nerve can be stimulated by any means known to those of skill in the art. Nonlimiting examples include: mechanical means such as a needle, ultrasound, or vibration. Mechanical stimulation can also be carried out by carotid massage, oculocardiac reflex, dive reflex and valsalva maneuver. The efferent vagal nerve fibers can also be stimulated by electromagnetic radiation such as infrared, visible or ultraviolet light; heat/cold exposure, magnetic field exposure, or any other energy source. The efferent vagus nerve can be stimulated by stimulating the entire vagus nerve (i.e., both the afferent and efferent nerves), or by isolating efferent nerves and stimulating them directly. The latter method can be accomplished by separating the afferent from the efferent fibers in an area of the nerve where both types of fibers are present. Alternatively, the efferent fiber is stimulated where no afferent fibers are present, for example close to the target organ served by the efferent fibers.

The efferent vagus nerve fibers can also be stimulated by stimulating the target organ directly, e.g., electrically, thus stimulating the efferent fibers that serve that organ. In other embodiments, the ganglion or postganglionic neurons of the vagus nerve can be stimulated. In preferred embodiments set forth herein, the vagus nerve is stimulated electrically, using any electrical means known to those of skill in the art. For example, commercial vagus nerve stimulators for use herein include the Cyberonics NCP®, the NEMOS® device for t-VNS, or a transcutaneous electrical nerve stimulation (TENS) unit, such as the TENS 7000 (Roscoe Medical, Strongsville, Ohio), and the like.

In combination with the methods provided herein, the amount of stimulation useful to inhibit cytokine storm, can be determined by the skilled artisan without undue experimentation. In one embodiment, to inhibit, reduce or treat cytokine storm, a constant voltage stimuli of about 1 to 5 V, at 2 ms and 1 Hz, for 10 minutes is contemplated herein to inhibit the systemic inflammatory cytokines sufficiently.

Figure 6:
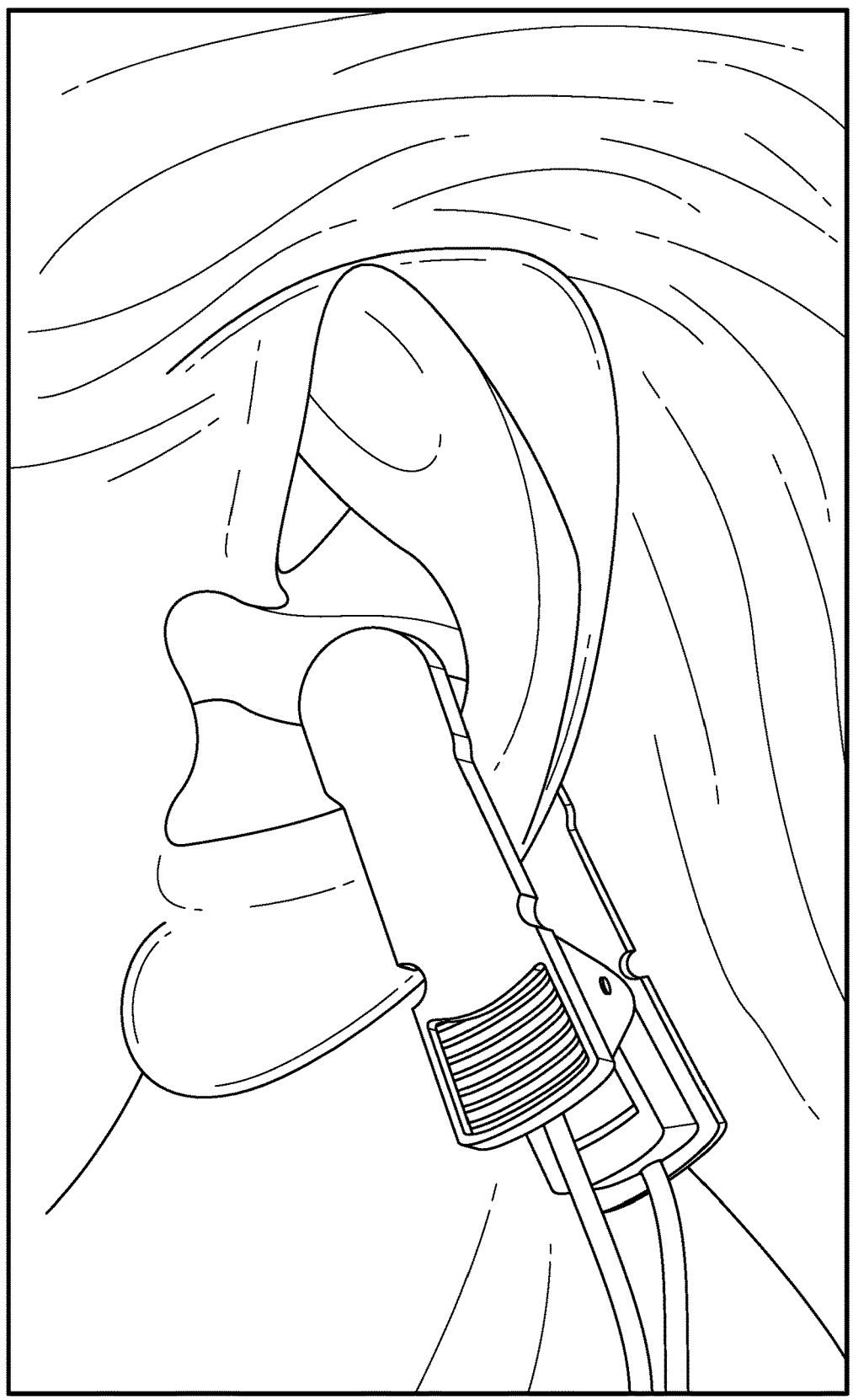
FIG. 6 shows a depiction of the of electrodes clipped across the concha to enable electrical stimulation.
Figure 7:
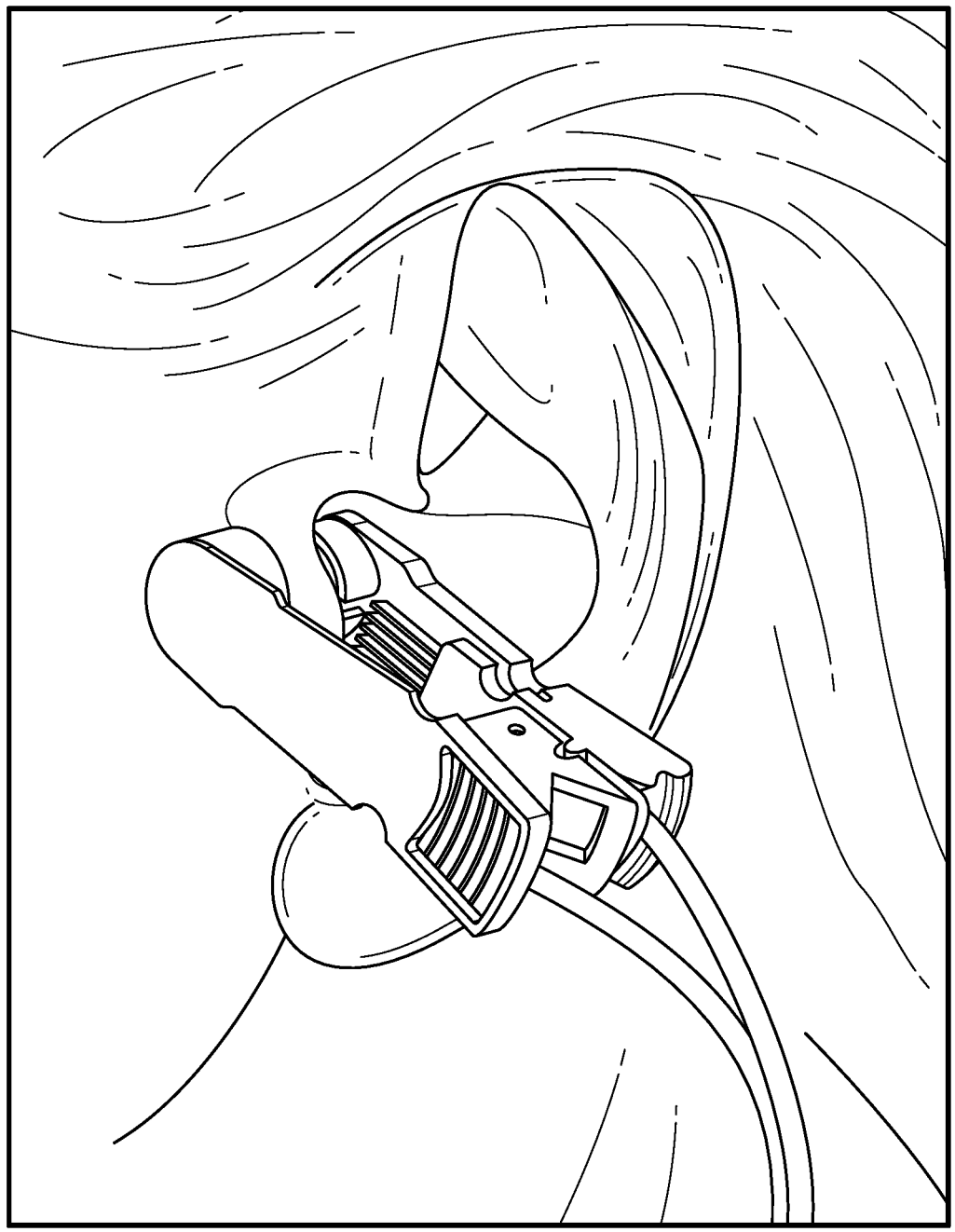
FIG. 7 shows a depiction of electrodes clipped across the tragus to enable electrical stimulation.

In certain embodiments, the electrical stimulation is achieved by clipping electrodes across the tragus (FIG. 7) or concha (FIG. 6) of the ear, inducing an electrical current with a TENS (transcutaneous electrical nerve stimulation) unit with the frequency in the range selected from about 0.1 Hz to about 30 Hz, about 0.3 Hz to about 25 Hz, about 0.5 Hz to about 20 Hz, about 0.7 Hz to about 15 Hz, about 0.9 Hz to about 10 Hz, about 1.0 Hz to about 9 Hz, about 1.2 Hz to about 8 Hz, about 1.4 Hz to about 7 Hz, about 1.6 Hz to about 6 Hz, or about 2 Hz to about 5 Hz. In other embodiments, the frequency is in the range selected from about 1 Hz to about 30 Hz, about 2 to about 25 Hz, about 3 to about 20 Hz, about 4 to about 15 Hz, and about 5 to about 10 Hz pulse frequency; with about 5 to about 10 Hz pulse frequency being most commonly used.

In these embodiments the pulse width can be in the range selected from about 20 to about 1000 uS, about 30 to about 900 uS, about 40 to about 800 uS, about 50 to about 700 uS, about 60 to about 600 uS, about 70 to about 500 uS, about 80 to about 450 uS, about 90 to about 400 uS, about 100 to about 350 uS, about 110 to about 325 uS, about 120 to about 300 uS, about 130 to about 275 uS, about 140 to about 260 uS, or about 150 to about 250 uS. In other embodiments, the pulse width can be in the range selected from about 100-800 µS, 125-750 µS, 150-700 µS, 175-650 µS, 200-600 µS, 225-550 µS and 250-500 µS pulse duration; with 250-500 µS pulse duration most commonly used.

In these embodiments, the current can be in a range selected from about 0.1 to about 5.0, about 0.2 to about 4.0, about 0.3 to about 3.0, about 0.4 to about 2.0, or about 0.5 to about 1.0 mAmps. In a particular embodiment, the electrical stimulation is achieved by inducing an electrical current with a TENS (transcutaneous electrical nerve stimulation) unit with the frequency at 5-10 Hz, pulse width at 100-800 uS and 0.5-1.0 mAmps. In another embodiment, a range of about 0.1 to about 4.8 mA output current is employed; and the currents are dosed between currents slightly below the perceptive threshold all the way up to the maximally tolerated current by the subject (with at or just below the perceptive threshold are most common).

It is contemplated herein, that the tVNS is employed for an amount of time sufficient to adequately reduce the pro-inflammatory cytokines via the cholinergic anti-inflammatory pathway. Suitable dosing regimens can range from a single 5-minute electrical impulse once daily to repeated 5-minutes impulses every 4-6 hours. In further embodiments, the electrical impulse or treatment can range from about 2 to 10 minutes, from about 3 to 8 minutes, from about 4 to 7 minutes, or about 5-6 minutes. In other embodiments, the individual stimulation doses can range from: about 30 sec to about 5 min; from about 45 sec to about 4.5 mins; about 1 min to about 4 min; about 1.5 to about 3.5 min; about 2 min to about 3 min. In other embodiments, the individual stimulation doses can range from: about 30 sec to about 5 min; from about 30 sec to about 4.5 mins; about 30 sec to about 4 min; about 30 sec to about 3.5 min; about 30 sec to about 3 min; about 30 sec to about 2.5 min; about 30 sec to about 2 min; about 30 sec. to about 1.5 min; about 30 sec to about 1 min; and the like. In yet further embodiments, the electrical impulses or treatments can be administered multiple times daily, such as once: every hour, every 2 hours, every 3 hours, every 4 hours, every 5 hours, every 6 hours, every 8 hours, every 10 hours, every 12 hours, or every 24 hours (e.g., once daily, and the like). In another embodiment, the number of doses or treatments per day can be selected from the group consisting of 1, 2, 3, 4, 5, 6, 7, 8, 9, 10, 11, 12, 13, 14, 15, 16, 17, 18, 19, 20 treatments per day.

The length of treatment can be as long as is necessary to achieve the effect of preventing, reducing or reversing cytokine storm in subject or patient; such as for example, from 1 to 30 days, 1 to 25 days, 1 to 20 days, 1 to 15 days, 1 to 10 days, 1 to 5 days. In a particular embodiment, the length of treatment is 14 days. In a particular embodiment, the subject receives 4, 5-minute treatments per day for 14 days.

In other embodiments, severe inflammatory states are contemplated herein to benefit from a continuous on-off cycling regimen with repetitive continuous electrical impulses (e.g., for 2 to 10 minutes, 5 minutes, or the like) followed by a 30-second to 5-minute off-phase (no current). For example, an on-off-on-off continuum for 24 hours per day, and the like. As other examples, this particular embodiment contemplates administering an electrical impulse once every 5.5. mins., 6.5 mins., 7 mins., 7.5 mins., 8 mins., 8.5 mins., 9 mins., 9.5 mins., 10 mins., 15 mins., 20 mins., 25 mins., 30 mins., 35 mins., 40 mins., 45 mins., 50 mins., 55 mins., and 60 mins. (e.g., every hour, and the like).

In a particular embodiment, the various elements of the electrical current used for inflammation modulation to prevent, reduce or reverse cytokine storm are:
- 1-30 Hz pulse frequency (5-10 Hz most commonly)
- 100-800 µS pulse duration (250-500 uS most commonly)
- 0.1-4.8 mA output current. Currents are dosed between to currents slightly below the perceptive threshold all the way up to the maximally tolerated current by the subject (at or just below the perceptive threshold are most common)
- 30-sec-5 min. individual stimulation doses
- 10-100 V voltage output
- Biphasic Waveform

EXAMPLES

Example 1—VNS Intervention Trial for COVID-19 Pneumonia—Single Arm, Non-Controlled, Open Label Study 50 Subjects Intervention
  In this study, 5-50 (e.g., 5, 10, 15, 20, 25, 30, 35, 40, 45, 50, or more) COVID-19 patients presenting pneumonia are treated with VNS intervention methods as described herein
  Routine care+taVNS 5 Hz, 800 mS at 10 v below perception threshold.
  Subjects receive 4, 5-minute treatments per day for 14 days.
Primary Outcome Measures
  Survival without need of mechanical ventilation at day 14 from symptom onset.
  WHO progression scale ≤5 at day 4 since admission
  Cumulative incidence of successful tracheal extubation (>48 h) at day 14 since admission
  WHO progression scale ≤7 at day 4 since admission
WHO progression scale:
0—Uninfected; no viral RNA detected
1—Asymptomatic; viral RNA detected
2—Symptomatic; independent
3—Symptomatic; assistance needed
4—Hospitalized; no oxygen therapy
5—Hospitalized; oxygen by mask or nasal prongs
6—Hospitalized; oxygen by NIV or High flow
7—Intubation and mechanical ventilation, pO2/FIO2>=150 or SpO2/FIO2>=200
8—Mechanical ventilation, (pO2/FIO2<150 OR SpO2/FIO2<200) or vasopressors (norepinephrine >0.3 microg/kg/min)
9—Mechanical ventilation, pO2/FIO2<150 and vasopressors (norepinephrine >0.3 microg/kg/min), or Dialysis or ECMO
10—Death Results—The intervention methods as described above are conducted on 5, 10, 15, 20, 25, 30, 35, 40, 45 or 50 subjects.

In one embodiment, the results indicate that an amount selected from: at least 20%, at least 30%, at least 40%, at least 50%, at least 60%, at least 70%, at least 80%, or at least 90% of the patients treated with VNS survived without need of mechanical ventilation at day 14 from symptom onset.

In another embodiment, the results indicate that an amount selected from: at least 20%, at least 30%, at least 40%, at least 50%, at least 60%, at least 70%, at least 80%, or at least 90% of the patients treated with VNS exhibited a cumulative incidence of successful tracheal extubation (>48 h) at day 14 since admission.

In another embodiment, the results indicate that of the hospitalized patients treated with VNS therapy, a reduction in mortality of hospitalized patients occurred in an amount selected from: at least 20%, at least 30%, at least 40%, at least 50%, at least 60%, at least 70%, at least 80%, or at least 90%.

What is claimed is:

1. A method for preventing, reducing or reversing cytokine storm in a subject in need thereof, said method comprising:
   administering to said subject vagus nerve stimulation (VNS), wherein the VNS is provided transcutaneously using electrical stimulation through an electrical current,
   wherein the electrical stimulation is achieved by clipping electrodes across the tragus or concha of an ear and inducing an electrical current with a transcutaneous electrical nerve stimulation (TENS) unit,
   wherein the electrical current has a frequency at 2-5 Hz, pulse width at 100-800 uS and 0.5-1.0 mAmps, and
   wherein the subject receives 4, 5-minute treatments per day for 14 days.

2. The method of claim 1, wherein the cytokine storm is caused by a condition selected from the group consisting of: a virus, bacteria, graft-versus-host disease, cytomegalovirus infection, Epstein-Barr virus-associated hemophagocytic lymphohistiocytosis, group A streptococcus, influenza virus, variola virus, severe acute respiratory syndrome coronavirus (SARS-CoV), multiple sclerosis, pancreatitis, multiple organ dysfunction syndrome, lung infections, gastrointestinal tract infections, urinary tract infections, central nervous system, infections, skin infections, joint spaces infections, or any substance that is foreign to the body.

3. The method of claim 1, wherein the cytokine storm is caused by SARS-COV2 infection.

\* \* \* \* \*